US00PP30515P3

(12) United States Plant Patent
Tsuiki

(10) Patent No.: US PP30,515 P3
(45) Date of Patent: May 21, 2019

(54) ***GAULTHERIA* PLANT NAMED 'HOKUTOTAKAJI-001'**

(50) Latin Name: *Gaultheria procumbens*
Varietal Denomination: Hokutotakaji-001

(71) Applicant: Tsukasa Tsuiki, Nanae (JP)

(72) Inventor: Tsukasa Tsuiki, Nanae (JP)

( * ) Notice: Subject to any disclaimer, the term of this patent is extended or adjusted under 35 U.S.C. 154(b) by 0 days.

(21) Appl. No.: 15/732,116

(22) Filed: Sep. 20, 2017

(65) Prior Publication Data

US 2019/0090398 P1 Mar. 21, 2019

(51) Int. Cl.

| | |
|---|---|
| ***A01H 5/00*** | (2018.01) |
| ***A01H 6/00*** | (2018.01) |
| ***A01H 5/02*** | (2018.01) |

(52) U.S. Cl.

USPC ..... Plt./226
CPC ..... *A01H 6/00* (2018.05); *A01H 5/02* (2013.01)

(58) Field of Classification Search

USPC ..... Plt./226
See application file for complete search history.

*Primary Examiner* — Susan McCormick Ewoldt
*Assistant Examiner* — Karen M Redden
(74) *Attorney, Agent, or Firm* — Barbara Campbell; Bethany Reid Roahrig; Cochran Freund & Young LLC

(57) ABSTRACT

A new cultivar of *Gaultheria procumbens* plant named 'Hokutotakaji-001' that is characterized by its compact, low-growing and weeping plant habit, glossy dark green and bronze colored foliage, clusters downward-facing bell-shaped white flowers held on orange-red stems and white berries which turn light pink in the winter.

4 Drawing Sheets

Genus and species: *Gaultheria procumbens.*
Variety denomination: 'Hokutotakaji-001'.

BACKGROUND OF THE NEW PLANT

The present invention relates to a new and distinct cultivar of *Gaultheria*, commonly known as Wintergreen, which is grown as an ornamental plant for use in containers and in the landscape. The new cultivar is known botanically as *Gaultheria procumbens* and will be hereinafter referred to by the denomination 'Hokutotakaji-001'.

During December 2009 to January 2010, the inventor observed within his crop of red-berried *Gaultheria procumbens* (species, unpatented) a naturally occurring whole-plant mutation which bore white-colored berries in the summer and which persist and develop light pink coloration in the winter months. The whole plant mutation was discovered by the inventor in the inventor's greenhouse in Nanae-town, Hokkaido, Japan. The mutation was observed as a single plant which was found growing in a commercial crop of unnamed red-berried *Gaultheria procumbens*. The species *Gaultheria procumbens* is widely cultivated as such (the species) and not as a named cultivar. The inventor also observed that the whole plant mutation exhibited additional desirable characteristics including large berries, weeping plant habit and smaller leaves which allow the berries to be more visible.

The inventor first propagated 'Hokutotakaji-001' in his greenhouse in Nanae-town, Hokkaido, Japan in June 2011 using the method of stem cuttings. The inventor has confirmed that 'Hokutotakaji-001' is stable and reproduces true to type in each successive generation of asexual reproduction.

CROSS-REFERENCE TO RELATED APPLICATIONS

A Plant Breeders Rights application was filed in Japan, application number 29854, on Jan. 9, 2015. The present variety has not been sold or made publicly available more than one year prior to the filing date of the instant application.

SUMMARY

The following traits have been repeatedly observed and represent the characteristics of the new *Gaultheria* cultivar 'Hokutotakaji-001'. These traits in combination distinguish 'Hokutotakaji-001' from all other varieties of *Gaultheria* known to the inventor. 'Hokutotakaji-001' has not been tested under all possible conditions and phenotypic differences may be observed with variations in environmental, climatic and cultural conditions.

1. 'Hokutotakaji-001' exhibits a compact, low-growing and weeping plant habit.
2. 'Hokutotakaji-001' exhibits glossy dark green foliage.
3. From around October to March, the emerging leaves of 'Hokutotakaji-001' develop a bronzed appearance.
4. In June and July, 'Hokutotakaji-001' exhibits clusters of downward-facing bell-shaped white-colored flowers and white berries which are held on orange-red stems.
5. From fall until spring (i.e. throughout winter) the white berries of 'Hokutotakaji-001' are persistent and develop a pink coloration.
6. The berries of 'Hokutotakaji-001' can achieve a diameter of 20 mm.
7. After 1 year of growth in a 9 cm container, a plant of 'Hokutotakaji-001' is 10 cm in height and 15 cm in width.
8. After 2 years of growth in a 13 cm container, a plant of 'Hokutotakaji-001' is 14 cm in height and 33 cm in width.

DESCRIPTION OF THE PHOTOGRAPHS

The accompanying color drawings illustrate the overall appearance of the plant and flowers of the new *Gaultheria* variety named 'Hokutotakaji-001'. The drawings have been made from digital photographs of plants of 'Hokutotakaji-001', which were grown in the inventor's unheated greenhouse in Nanae-town, Hokkaido, Japan.

DESCRIPTION OF THE NEW VARIETY

Figure 1:
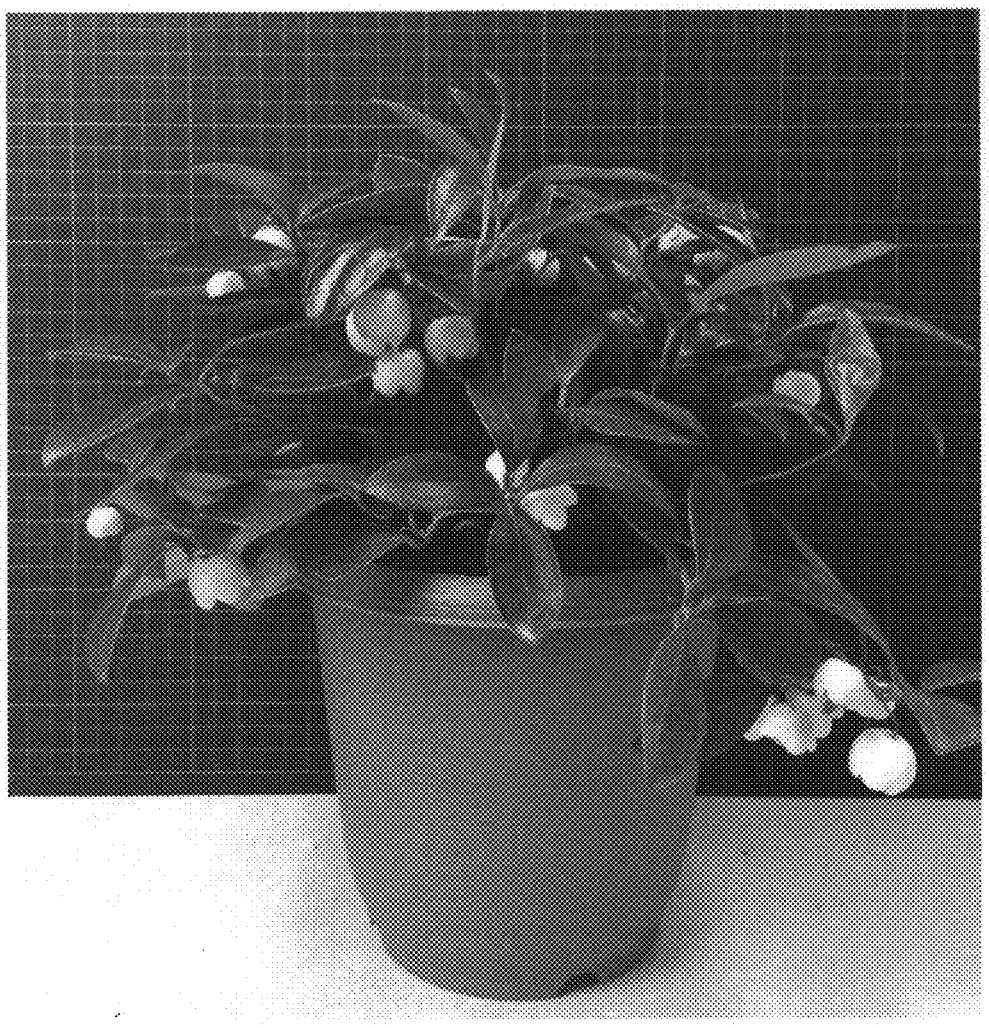
FIG. 1 depicts a two-year old plant of 'Hokutotakaji-001' in early summer and illustrates the downward-facing white flowers and the bronzed coloration of recently-emerged leaves.
Figure 2:
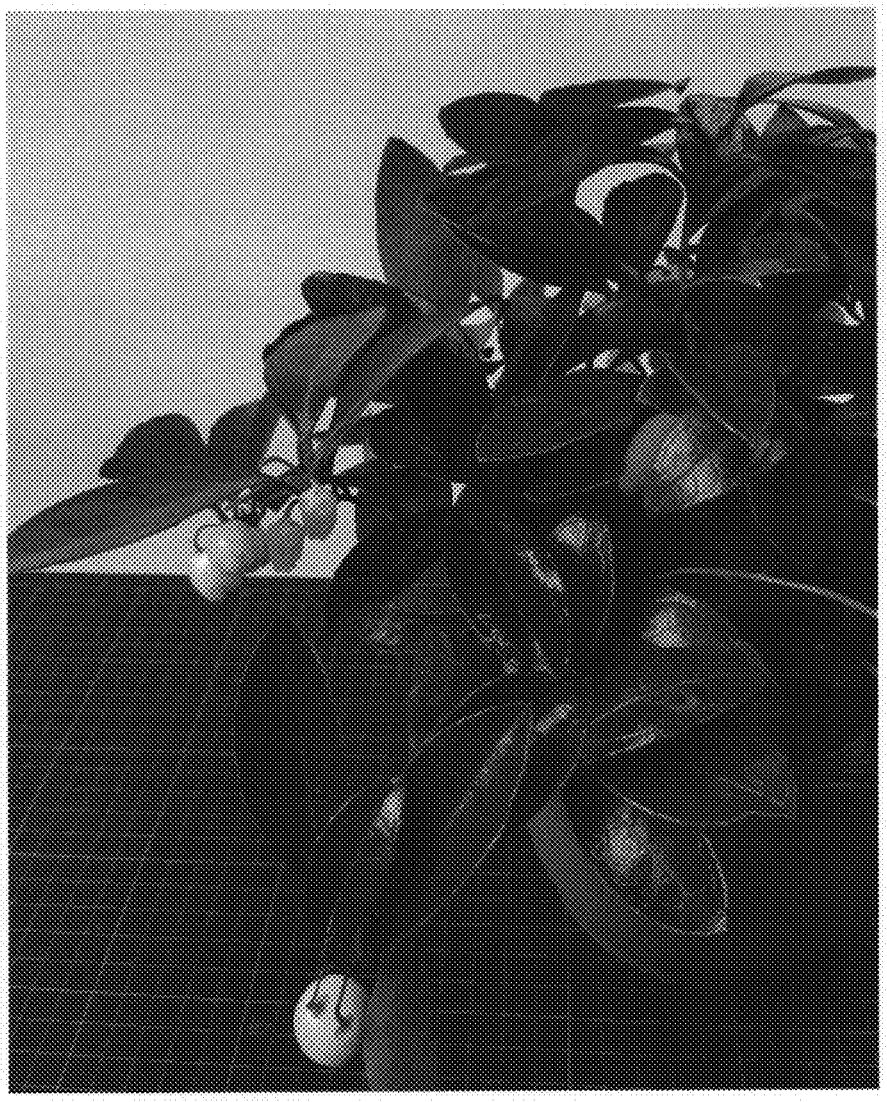
FIG. 2 depicts a close-up view of the dark green and bronze colored foliage together with the last flowers and the first fruits (berries) of the season.
Figure 3:
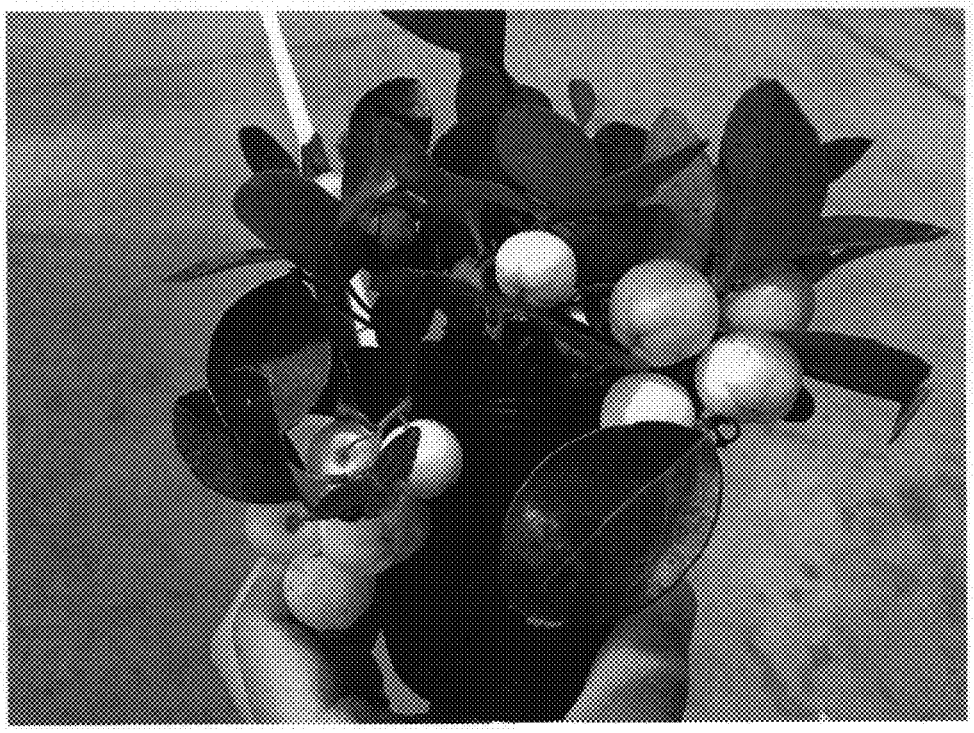
FIG. 3 depicts the first onset of pink coloration of the berries in early winter.
Figure 4:
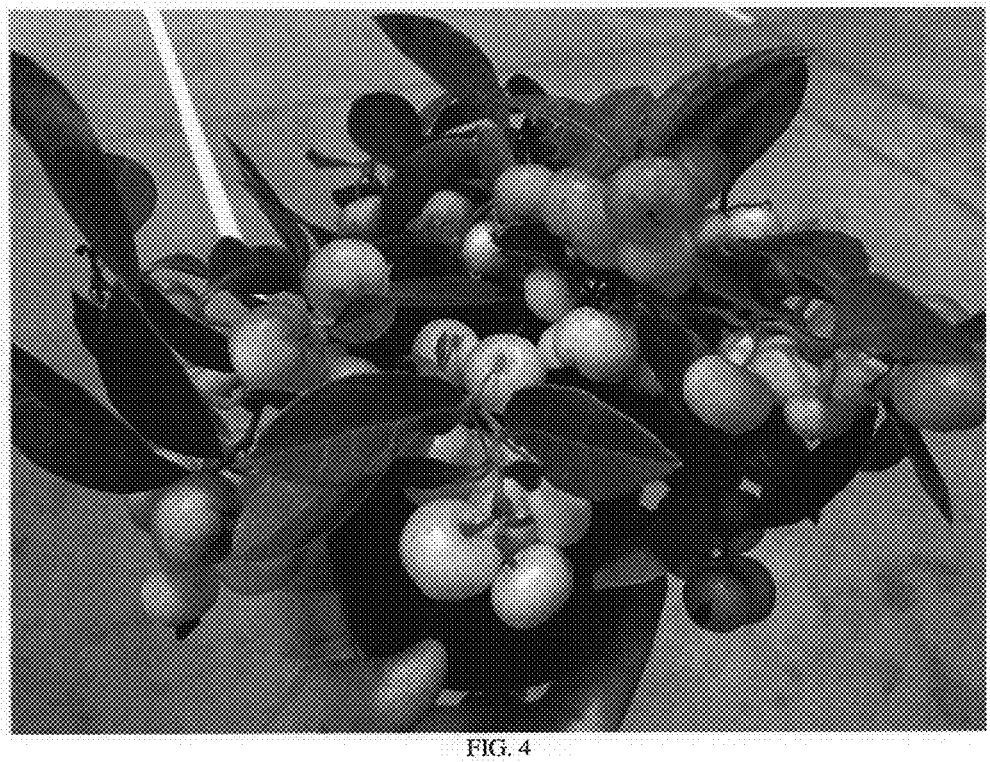
FIG. 4 depicts the eventual pink coloration of the berries in midwinter.

The following is a detailed description of *Gaultheria procumbens* 'Hokutotakaji-001' which has been grown and observed by the inventor in Hokkaido, Japan. The observed plants were two years old.

The color determinations are in accordance with the 2007 edition of The Colour Chart of the Royal Horticultural Society London, England, except where color terms of ordinary dictionary significance are used. Growing conditions, diseases and pests are similar to that of other *Gaultheria*.

Plant description:

- *Botanical classification.*—*Gaultheria procumbens* 'Hokutotakaji-001'.
- *Commercial classification.*—Hardy groundcover shrub.
- *Use.*—For use in containers, and in the landscape as a border plant or as a groundcover.
- *Parentage.*—Selected as a white-berried seedling from red-berried seedlings of the species *Gaultheria procumbens*.
- *Bloom period.*—June and July.
- *Plant habit.*—Clumping, low growing, weeping.
- *Vigor.*—Moderate.
- *Dimensions.*—Height: 14 cm. Width: 33 cm.
- *Hardiness.*—The typical hardiness of the species is USDA Zone 3. 'Hokutotakaji-001' has not been tested in temperatures below USDA Zone 5.
- *Propagation method.*—Internodal stem cuttings with leaves attached.
- *Root system.*—Fibrous.
- *Cultural requirements.*—'Hokutotakaji-001' prefers ericaceous potting medium and planting soils. Light shade to full shade preferred.
- *Growing time.*—'Hokutotakaji-001' may be sold as a one-year old plant with occasional flowers and berries. A two-year old plant of 'Hokutotakaji-001' will carry numerous flowers and berries.
- *Pests and diseases.*—No pests or diseases have been observed to affect 'Hokutotakaji-001'.
- *Branches* (*quantity*).—From 15 to 18 basal and lateral branches.

Stem:

- *Stem color.*—182D.
- *Stem length.*—70 mm to 80 mm.
- *Stem diameter.*—3 mm.
- *Internode distance.*—5 mm to 10 mm.
- *Stem texture.*—Smooth, semi-glossy with very light pubescence.

Foliage:

- *Quantity* (*leaves on one stem*).—8 to 10.
- *Leaf arrangement.*—Alternate.
- *Leaf length.*—40 mm.
- *Leaf width.*—25 mm.
- *Leaf color* (*mature leaves year-round, upper surface*).—Green, 139A to 139B.
- *Leaf color* (*mature leaves year-round, lower surface*).—Green, ranges between 146C and 152D.
- *Leaf color* (*immature leaves, October through March, upper surface*).—Bronze, 59A.
- *Leaf color* (*immature leaves, October through March, lower surface*).—Bronze, 180B.
- *Leaf shape.*—Elliptic.
- *Leaf base.*—Attenuate.
- *Leaf apex.*—Acute
- *Leaf margin.*—Serrate.
- *Leaf surface.*—Smooth, glossy (upper surface).
- *Leaf surface.*—Matte (lower surface).
- *Leaf venation pattern.*—Pinnate.
- *Leaf veins color* (*green leaves, both surfaces*).—146D.
- *Leaf veins color* (*bronze leaves, both surfaces*).—185C.
- *Leaf fragrance.*—Wintergreen mint fragrance when crushed.

Petioles:

- *Petiole shape.*—Round.
- *Petiole length.*—7 mm to 8 mm.
- *Petiole width.*—2 mm.
- *Petiole color.*—183D.
- *Petiole surface.*—Smooth, glossy.

Inflorescence:

- *Inflorescence type.*—Panicle.
- *Inflorescence length* (*height*).—25 mm to 35 mm.
- *Inflorescence width.*—15-20 mm.
- *Number of inflorescences in one plant.*—8 to 10.
- *Number of flowers in one inflorescence.*—Up to 5.
- *Inflorescence fragrance.*—None.

Flower buds:

- *Flower buds, shape.*—Obovate.
- *Flower buds, length.*—7 mm to 10 mm.
- *Flower buds, diameter.*—6-8 mm.
- *Flower buds, color.*—Ranges between NN155D and 155A.

Corolla, petals:

- *Corolla shape.*—Urceolate.
- *Petal arrangement.*—5 to 6 petals, fused longitudinally, apex free, recurving.
- *Petal shape.*—Oblanceolate.
- *Petal length.*—12 mm to 16 mm.
- *Petal width.*—6 mm to 8 mm.
- *Petal color.*—Ranges between NN155D and 155A.
- *Petal surface.*—Translucent, glossy.

Calyx, sepals:

- *Calyx diameter.*—8 mm to 10 mm.
- *Calyx length* (*height*).—3 mm to 4 mm.
- *Sepal quantity.*—5 to 6.
- *Sepal shape.*—Broadly triangular, apex acute.
- *Sepal length.*—4 mm to 5 mm.
- *Sepal width.*—3 mm.
- *Sepal color.*—NN155C.
- *Sepal surface.*—Smooth, slightly glossy. Opaque.

Peduncle:

*Peduncle length.*—45 mm.

*Peduncle width.*—1 mm to 2 mm.

*Peduncle color.*—173A to 173B.

*Peduncle surface.*—Puberulent.

Pedicel:

*Pedicel length.*—16 mm.

*Pedicel diameter.*—1.5 mm.

*Pedicel color.*—34A changing abruptly to 162D towards calyx.

*Pedicel surface.*—Puberulent.

Reproductive organs:

*Stamen.*—10 to 12 in number.

*Filament length.*—4 mm, diameter is less than 0.5 mm.

*Filament color.*—NN155C.

*Anthers.*—Oblong, 3 mm in length, dark brown.

*Pollen quantity.*—Low.

*Pollen color.*—N167B.

*Pistil quantity.*—1.

*Stigma shape.*—Truncate.

*Style length.*—4 mm.

*Style color.*—155C.

Fruit (berries):

*Berry quantity per branch.*—Up to 5.

*Berry shape.*—Globose (flattened at apex), formed of 5 to 6 lobes, apex depressed and surrounded by deltoid lobe apices.

*Berry dimensions.*—Mature berries range between 11 mm in diameter, 9 mm to 10 mm in height and 20 mm in diameter, 18 mm in height. The preponderance of mature berries are close to 20 mm in diameter and 18 mm in height.

*Berry color.*—NN155D in summer months, persistent and becoming 67C in winter months.

*Berry surface.*—Glossy, glabrous.

Seed:

*Description.*—Minute, irregular, color 21C.

COMPARISON TO PARENTAL LINE AND TYPICAL VARIETIES

Whereas 'Hokutotakaji-001' bears white berries with light pink coloration in winter, the parent from which 'Hokutotakaji-001' was raised bears red berries. The parent is itself a naturally-occurring whole-plant mutation of a plant of the red-berried species, *Gaultheria procumbens*.

Whereas 'Hokutotakaji-001' bears white berries with light pink coloration in winter, other varieties of *Gaultheria* known to the inventor bear red berries. The inventor is not aware of other white berried varieties of *Gaultheria* which exhibit pink coloration in winter. In addition, in comparison with other varieties of *Gaultheria* known to the inventor, or in comparison with the species which is widely grown, the inventor considers that 'Hokutotakaji-001' exhibits large berries, a weeping habit and bears smaller leaves, which allow better visibility of the white or light pink berries.

I claim:

1. A new and distinct variety of *Gaultheria* plant named 'Hokutotakaji-001' as illustrated and described herein.

* * * * *